United States Patent [19]

Jirkovsky

[11] Patent Number: 4,778,812

[45] Date of Patent: Oct. 18, 1988

[54] 2,3-DIHYDRO-9-METHYL-1H-PYR-ROLO[1,2-A]INDOL-1-AMINES AND DERIVATIVES THEREOF

[75] Inventor: Ivo L. Jirkovsky, Plainsboro, N.J.

[73] Assignee: American Home Products Corporation, New York, N.Y.

[21] Appl. No.: 61,836

[22] Filed: Jun. 12, 1987

[51] Int. Cl.$^4$ .................. C07D 487/04; A61K 31/445; A61K 31/40

[52] U.S. Cl. ..................................... 514/323; 514/411; 546/272; 548/428

[58] Field of Search .................... 546/272; 548/428; 514/411, 323

[56] References Cited

U.S. PATENT DOCUMENTS

| | | | |
|---|---|---|---|
| 3,206,470 | 9/1965 | Allen | 260/319 |
| 4,624,954 | 11/1986 | Jirkovsky | 514/290 |

OTHER PUBLICATIONS

Kobayashi et al, Chem. Abs. 85, 177288 (1976).
P. Hoechst et al, Arch. Pharmaz., 308, 779 (1975).
G. R. Allen et al, J. Org. Chem., 30, 2904 (1965).
W. A. Remers et al, J. Org. Chem., 30, 2910 (1965).
G. Leadbetter et al, J. Org. Chem., 39, 3580 (1974).
J. Mott, J. Med. Chem., 21, 493 (1978).

*Primary Examiner*—Mark L. Berch
*Attorney, Agent, or Firm*—Walter Patton

[57] ABSTRACT

Herein is disclosed 2,3-dihydro-9-methyl-1H-pyrrolo[1,2-a]indol-1-amines and derivatives, therapeutically acceptable acid addition salts thereof, processes for their preparation, methods of using the derivatives, and pharmaceutical compositions. The derivatives are chemically novel agents with antihypoxic, cerebroactive, and cognition activating properties.

7 Claims, No Drawings

2,3-DIHYDRO-9-METHYL-1H-PYRROLO[1,2-A]INDOL-1-AMINES AND DERIVATIVES THEREOF

BACKGROUND OF THE INVENTION

1. Field of the Invention

This invention relates to novel 2,3-dihydro-9-methyl-1H-pyrrolo[1,2-a]indol-1-amines and derivatives thereof, to therapeutically acceptable acid addition salts thereof, to processes for their preparation, to methods of using the derivatives and to pharmaceutical compositions of the derivatives. These derivatives have antihypoxic, cerebroactive, and cognition activating properties.

2. Description of Related Art

The closest related art is U.S. Pat. Nos. 3,206,470 and 4,624,954.

U.S. Pat. No. 3,206,470 discloses pyrrolo[1,2-a]indoles, having antimicrobial activity, differing from those of the present invention by having a substituent other than hydrogen at the 7-position. At the 9-position the compounds of the present invention are substituted with an alkyl group not disclosed in the prior art.

U.S. Pat. No. 4,624,954 discloses 6,7,8,9-tetrahydro-10-methylpyrido[1,2-a]indol-1-amines having cerebroactive and cognition activating properties.

Other related art is

P. Hoeschst et al, Arch. Pharmaz., 308, 779 (1975);
G. R. Allen et al, J. Org. Chem., 30, 2904 (1965);
W. A. Remers et al, J. Org. Chem., 30, 2910 (1965);
G. Leadbetter et al, J. Org. Chem., 39, 3580 (1974); and
J. Mott, J. Med. Chem., 21, 493 (1978).

SUMMARY OF THE INVENTION

The compounds of this invention are represented by formula (I)

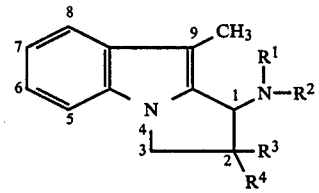

wherein $R^1$ and $R^2$ are independently selected from the group consisting of hydrogen, lower alkyl containing 1 to 4 carbon atoms, or $R_1$ and $R_2$ are joined together to form a heterocyclic amine radical, selected from the group consisting of pyrrolidinyl and piperidinyl; $R^3$ and $R^4$ represent hydrogen or lower alkyl containing 1 to 4 carbon atoms; and the pharmaceutically acceptable acid addition salts thereof.

A preferred group of compounds of this invention is represented by formula (I) in which $R^1$ and $R^2$ are independently hydrogen, methyl, ethyl, propyl, or isopropyl; or $R^1$ and $R^2$ are joined together to form pyrrolidinyl, or piperidinyl; $R^3$ and $R^4$ are methyl; and the pharmaceutically acceptable acid addition salts thereof.

A still further preferred group of compounds of this invention is represented by formula (I) in which $R^1$ and $R^2$ are hydrogen or methyl; or $R^1$ and $R^2$ are joined together to form pyrrolidinyl; $R^3$ and $R^4$ are both methyl; and the pharmaceutically acceptable acid addition salts thereof.

The most preferred compounds of the present invention are designated 2,3-dihydro-2,2,9-trimethyl-1H-pyrrolo[1,2-a]indol-1-amine hydrochloride; 2,3-dihydro-2,2,9-trimethyl-1-(1-pyrrolidinyl)-1H-pyrrolo[1,2-a]indole hydrochloride; and the pharmaceutically acceptable acid addition salts thereof.

The compounds of formula (I) or a therapeutically acceptable acid addition salt thereof can be prepared by Scheme 2 or 3 set forth herein.

Both Scheme 2 and 3 utilize the intermediate ketone (II) (prepared according to the process of P. Hoechst et al, Arch. Pharmaz., 308, 779 (1975) illustrated in Scheme 1.

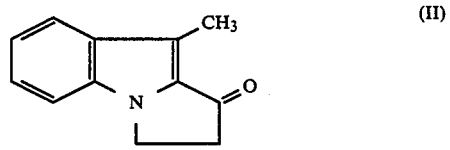

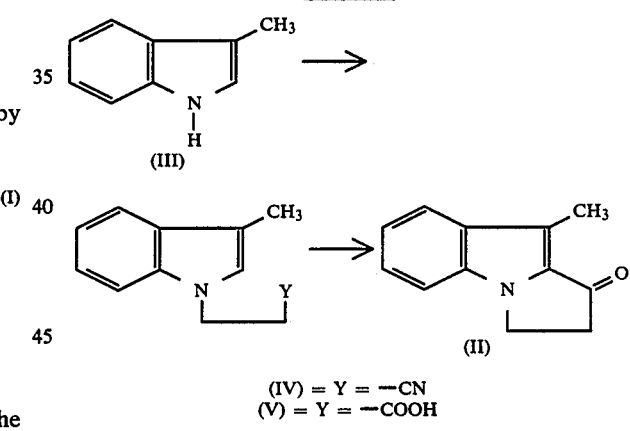

$(IV) = Y = -CN$
$(V) = Y = -COOH$

Referring to Scheme 1, addition of acrylonitrile to 3-methylindole (III) is followed by basic hydrolysis, and the resultant carboxylic acid (Y=—COOH) is cyclized using phosphorus pentoxide in refluxing xylene. The reported yield of the last step is 14%. According to the present invention, this cyclization was effected by polyphosphoric acid at 90° C., and the yield was improved to 54%.

Scheme 2

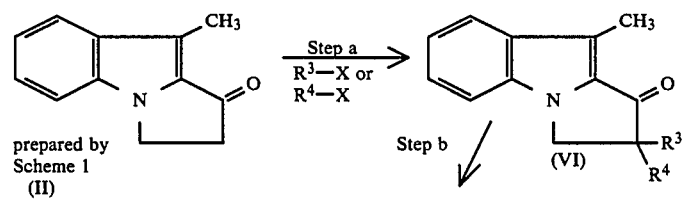

Scheme 2

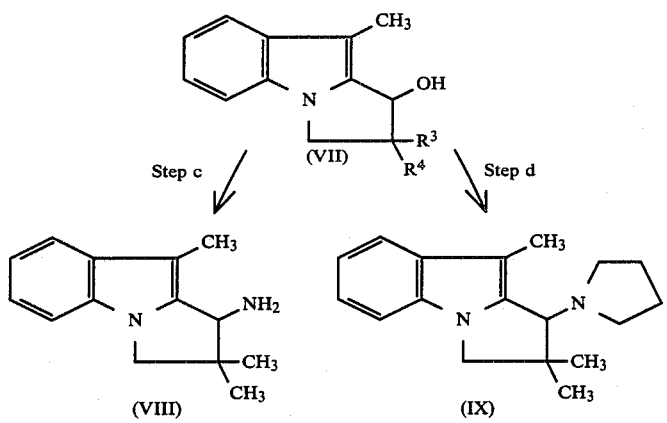

Referring to Scheme 2 in step (a) treatment of (II) with sodium hydride in dimethylformamide, followed by $R^3$-X, $R^4$-X provides the compound of formula (VI). In step (b) reduction of (VI) with sodium borohydride in methanol provides the corresponding alcohol (VII). In step (c) treatment of the alcohol (VII) with 2 moles of mesyl chloride in pyridine (excess), followed by addition of an excess (20–40 moles) of pyrrolidine or piperidine provides the compound of formula (I) wherein $R^1$ and $R^2$ are —H. In step (d) treatment of (VII) with thionyl chloride followed by pyrrolidine provides the compound of formula (I) wherein $R^1$ and $R^2$ are joined to form pyrrolidine.

Scheme 3 illustrates the process for the production of compounds of formula (I) wherein $R^3$ and $R^4$ are both hydrogen.

Scheme 3

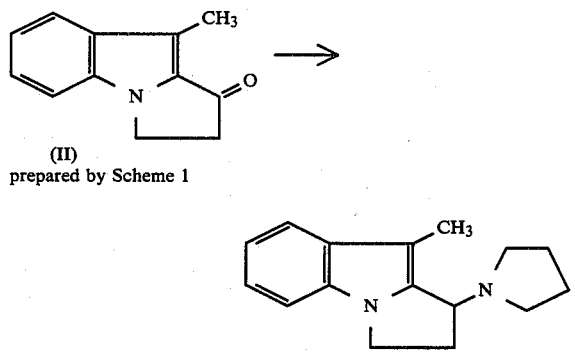

Referring to Scheme 3, this one-step reductive amination process using pyrrolidine and sodium cyanoborohydride in the presence of HCl according to the process reported by J. Mott et al, in J. Med. Chem., 21, 493 (1978) is used for the preparation of compounds of formula (I) wherein $R^3=R^4=$—H.

The compounds of formula (I) can be reacted with a therapeutically acceptable acid to obtain the corresponding compound of formula (I) as the salt with the therapeutically acceptable acid.

A pharmaceutical composition is provided by combining the compound of formula (I), or a therapeutically acceptable acid addition salt thereof, and a pharmaceutically acceptable carrier.

The compounds of this invention have antihypoxic, cerebroactive, and cognitive activating properties which can be used to treat a variety of learning, memory and attentional disorders in mammals by administering to the mammal with or without cerebral ischemia an effective amount of a compound of formula (I) or a therapeutically acceptable acid addition salt thereof.

DETAILED DESCRIPTION OF THE INVENTION

The term "lower alkyl" as used herein means straight and branched chain alkyl radicals containing from one to four carbon atoms, and includes methyl, ethyl, propyl, 1-methylethyl, butyl, 1,1-dimethylethyl, and the like, unless stated otherwise.

The term "halogen" as used herein means halogen radicals and includes fluoro, chloro, bromo and iodo, unless stated otherwise.

The compounds of this invention are capable of forming acid addition salts with therapeutically acceptable acids. The acid addition salts are prepared by reacting the base form of the appropriate compound of formula (I) with one or more equivalents, preferably with an excess, of the appropriate acid in an organic solvent, for example, diethyl ether or an ethanol diethyl ether mixture.

These salts, when administered to a mammal, possess the same or improved pharmacologic activities as the corresponding bases. For many purposes it is preferable to administer the salts rather than the basic compounds. Suitable acids to form these salts include the common mineral acids, e.g. hydrohalic, sulfuric or phosphoric acid; the organic acids, e.g. ascorbic, citric, lactic, aspartic or tartaric acid or their aqueous solutions whose pH has been adjusted to 5.5 or less; and acids which are sparingly soluble in body fluids and which impart slow-release properties to their respective sals, e.g. pamoic or tannic acid or carboxymethyl cellulose. The preferred salt is the hydrochloride salt. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The compounds of formula (I) are chemically novel agents with cerebroactive and cognition activating properties. They protect against anoxia-induced lethality in mice, and have also been shown to protect against experimentally-induced learning impairments, and to promote memory retrieval, and to enhance the rate of learning in rats. Compounds of formula (I) enhance vigilance in rats, as indicated by changes in the electrocorticogram. At the same time compounds of formula (I) are free from undesireable psychostimulating side effects.

COGNITION ACTIVATING PROPERTIES

Cognition (i.e., intellectual and memory function) is difficult to define in experimental terms and particularly so in preclinical pharmacological models. In attempts to measure the cognition activating properties of the compounds of formula (I) in rodents, the compounds have been investigated for their ability to protect against the physical consequences of anoxia, and to correct impaired memory in simple learning tests.

To test the protective ability of the compounds of formula (I) against the physical consequences of anoxia, mice were exposed to an atmosphere of pure nitrogen which killed all of the animals. Intraperitoneal pretreatment of mice with the compounds of formula I protected them against this lethal effect.

The data from this anoxia-induced lethality experiment demonstrates that compounds of formula I protect the brain against the consequences of anoxia.

CLINICAL UTILITY

The preclinical pharmacologic profile of the compounds of formula (I) suggests them to be novel and useful cognition activating agents. Therefore they are useful in the clinical treatment of a variety of learning, memory, and attentional disorders such as, minor impairments of memory fairly common with advancing age, and more fundamental cognitive changes associated with stroke, trauma, transient ischemic attacks, multi-infarct dementia, delirium, dementia, Alzheimer's disease, senile dementia of the Alzheimer's type (SDAT), amnestic syndromes, intoxication and withdrawal. Compounds of formula (I) are useful in the treatment of cognitive impairment in Parkinsonian and schizophrenic patients (referred to as subcortical dementias), although in these instances the dementia is perhaps secondary to a primary neurological defect. In children and young adults, treatment of dyslexia and attentional deficit disorder (ADD) may be enhanced by agents with the pharmacologic properties of the compounds of formula (I). Cognitive deficits in youngsters with mental deficits secondary to cerebral anoxia at birth e.g. cerebral palsy may be treated with compounds of formula (I). Cognitive deficits resulting from fetal alcohol syndrom may also respond to treatment with compounds of formula (I).

Clinical evidence and laboratory studies suggest that the cognitive defects of Alzheimer's disease are due, in part, to a loss of functioning of cholinergic neurons in the brain. As disclosed, compounds of formula (I) prevent behavioral impairment by the cholinergic receptor antagonist scopolamine. Thus, compounds of formula (I) are useful as protection against at least some of the behavioral effects produced by a hypofunctioning cholinergic state.

The useful dose range of the compounds of structure (I) in humans is in the range of about 1 to 300 mg/day taken in one or several doses.

The compounds of formula (I) of this invention are used alone or in combination with pharmacologically acceptable carriers, the proportion of which is determined by the solubility and chemical nature of the compound, chosen route of administration and and standard medical practice. For example, they are administered orall in the form of capsules, tablets, suspensions or solutions or they may be injected parenterally. Capsules and tablets are the preferred mode of administration. For parenteral administration they can be used in the form of a sterile solution containing other solutes, for example, enough saline or glucose to make the solution isotonic.

The capsule and tablet compositions contain the active ingredient in admixture with non-toxic pharmaceutical excipients known to be suitable in the manufacture of capsules and tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula (I) contain the active ingredient in admixture with one or more non-toxic pharmaceutical excipients known to be suitable in the manufacture of aqueous suspensions. Suitable excipients are, for example methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil for example, arachis oil, olive oil, sesame oil, or coconut oil, or in mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula (I) as cerebroactive and cognition activating agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective amount of the compounds for oral administration can usually range from about 1 to 300 mg/day in single or divided doses although as aforementioned variations will occur. However, a dosage level that is in the range of from about 1 to 150 mg/day in single or divided doses is employed most desirably for oral administration in order to achieve effective results.

The compounds of formula (I) also can be used to produce beneficial effects in the treatment of affective disorders, subcortical dementias, and related disorders when combined with a second therapeutic agent comprising a therapeutically effective amount of antidepressant, anxiolytic, anti-parkinsonism or neuroleptic compound commonly used as psychotherapeutic agent.

The compounds of this invention possess an assymetric carbon atom at position 1 and thus are made as racemic mixtures. The d and l enantiomorphs in these racemic mixtures can be separated via standard techniques such as fractional crystallization with d-tartaric acid, l-tartaric acid, l-quinic acid, and the like followed by basification and extraction of the active d or l enantiomorph free base.

The following examples are provided merely to illustrate the methods of preparation of the compounds of the present invention. These examples are not meant to be considered, in any way, as limitations of the breadth and scope of the present invention. The temperatures expressed in these examples are in degrees centigrade.

EXAMPLE 1

2,3-Dihydro-2,2,9-trimethyl-1-(1-pyrrolidinyl)pyrrolo[1,2-a]indole Hydrochloride

[(I): $R^1$ and $R^2$=1-pyrrolidinyl]

Step (1) Preparation of 2,3-Dihydro-9-methyl-1H-pyrrolo[1,2-a]indol-1-one

A mixture of 3-(methylindol-1-yl)propionic acid, prepared according to P. Hoechst, Arch. Pharmaz., 308, 779 (1975), (8.485 g, 41.8 mmole), and polyphosphoric acid (90 g) was heated to 90° C. under mechanical stirring in an open beaker for 1 hour, cooled to 60° C., and poured into ice water (200 mL). The organic products were extracted with ether (3×80 mL). The combined organic layer was washed with sat'd sodium carbonate (2×60 mL), separated, dried over MgSO$_4$, filtered, and evaporated. The residue was chromatographed on silica gel (240 g). Elution with 30% hexane/chloroform afforded 4.21 g, 55% of product, m.p. 173.5°–175° C., as yellow needles.

NMR (CDCl$_3$): δ 2.65 (s, 3H, CH$_3$-9), 3.25 (t, J=6.4 Hz, 2H, H-2), 4.45 (t, J=6.4 Hz, 2 H, H-3), 7.11–7.49 (m, 3H, Ar-H), 7.8 (d, J=8 Hz, 1H, H-8).

MS (relative intensity, fragment) m/e: 185 (100, M+), 184 (50, M-H), 157 (52, loss of ethylene).

Step (2) Preparation of 2,3-Dihydro-2,2,9-trimethyl-1H-pyrrolo[1,2-a]indol-1-one Sodium hydride (440 mg, 10 mmole, ~60% in mineral oil) was added portionwise at 25° C. to a solution of 2,3-dihydro-9-methyl-1H-pyrrolo[1,2-a]indol-1-one (930 mg, 5 mmole) in distilled dimethylformamide (20 mL). Under exclusion of moisture, the reaction mixture was stirred at 25° C. for 1 hour. Methyl iodide (1.56 g, 11 mmole) was added dropwise upon mild cooling. The mixture was stirred an additional 2 hours at 25° C., evaporated to dryness in vacuo. The residue was suspended in water (70 mL) and extracted with chloroform (2×75 mL). The combined organic layers were washed with brine (70 mL), dried over MgSO$_4$, filtered, and evaporated to dryness. The residue (1.28 g) was chromatographed on silica gel (45 g). Elution with 50% hexane/chloroform afforded 713.5 mg (67%) of product, m.p. 65.5°–67.5° C., as a light beige solid.

NMR (CDCl$_3$): δ 1.38 (s, 6H, gem CH$_3$), 2.58 (s, 3H, CH$_3$-9), 4.14 (s, 2H, H-3), 7.20–7.35 (m, 3H, Ar-H), 7.72 (d, J=8 Hz, 1H, H-8).

MS (relative intensity, fragment) m/e: 213 (56, M+), 198 (38, M-CH$_3$), 157 (100, loss of isobutylene).

Step (3) Preparation of 2,3-Dihydro-2,2,9-trimethyl-1H-pyrrolo[1,2-a]indol-1-ol

Sodium borohydride (1.93 g, 50.7 mmole) was added portionwise upon mild cooling to a solution of 2,3-dihydro-2,2,9-trimethyl-1H-pyrrolo[1,2-a]indol-1-one (3.62 g, 16.9 mmole) in methanol (80 mL). The reaction mixture was stirred at 25° C. overnight. The solvent was removed in vacuo, and the residue was suspended in water (80 mL). The product was extracted with chloroform (3×50 mL). The combined organic layers were washed with brine (50 mL), then dried over MgSO$_4$, filtered, and evaporated to dryness in vacuo to afford 3.49 g (96%) of product, m.p. 82°–85° C., as a light amber solid.

NMR (CDCl$_3$): δ 1.14 and 1.30 (singlets, 3H+3H, gem. CH$_3$), 1.56 (d, J=6Hz, 1H, OH), 2.38 (s, 3H, CH$_3$-9), 3.75 and 3.92 (doublets, J$_{gem}$=10 Hz, 1H+1H, H-3), 4.74 (d, J=6 Hz, 1H, H-1), 7.08–7.30 (m, 3H, Ar-H), 7.60 (d, J=8 Hz, 1H, H-8).

Step (4) Preparation of 2,3-Dihydro-2,2,9-trimethyl-1(1-pyrrolidinyl)pyrrolo[1,2-a]indole Hydrochloride Thionyl chloride (1.572 g, 13.2 mmole) was added to a solution of 2,3-dihydro-2,2,9-trimethyl-1H-pyrrolo[1,2-a]indol-1-ol (2.58 g, 12 mmole) in benzene (150 mL). The mixture was refluxed for 15 minutes, evaporated to dryness in vacuo, and the residue stripped with benzene (3×60 mL). The residue was dissolved in distilled tetrahydrofuran (150 mL). At 0° C. a solution of anhydrous pyrrolidine (1.872 g, 26.4 mmole) in tetrahydrofuran (30 mL) was added dropwise. The reaction mixture was stirred at 25° C. under exclusion of moisture for 48 hours. The solvent was removed in vacuo, and the residue partitioned between water (200 mL) and ether (300 mL). The separated organic layer was extracted with 1–2% hydrochloric acid (2×150 mL). The combined aqueous layers were basified with sodium carbonate and extracted with toluene (3×120 mL). The combined organic layers were dried over MgSO$_4$, filtered, and evaporated to afford 1.49 g (46%) of product. The monohydrochloride salt was prepared in acetonitrile with ethereal hydrochloric acid, and recrystallized from ethanol/ether, m.p. 205°–206° C., as a light beige powder.

IR (KBr): 3420 (broad, 2950, 2520, 2440, 1460 cm$^{-1}$.
UV (MeOH): λmax 277 nm/ε=7484.
NMR (DMSO-d$_6$): δ 0.91 and 1.51 (singlets, 3H+3H, gem. CH$_3$), 1.75–2.05 (m, 4H, CH$_2$), 2.33 (s, 3H, CH$_3$-9), 2.72 (m, 1H, N-CH), 3.25–3.50 (m, 3H, N-CH$_2$), 3.75 (m, 1H, N—CH), 3.79 and 4.22 (doublets, J$_{gem}$=11.8 Hz, 1H+1H, H-3), 4.68 (d, J=4 Hz, 1H, H-1), 7.05 (t, J=8 Hz, 1H, H-7), 7.18 (t, J=8 Hz, 1H, H-6), 7.32 (d, J=8 Hz, 1H, H-5), 7.56 (d, J=8 Hz, 1H, H-8).
MS (relative intensity, fragment) m/e: 268 (38, M+), 212 (100, M-isobutylene), 198 (28, M-pyrrolidine).
Calculated: C, 70,92%; H, 8.26%; N, 9.19%. Found: C, 70.46%; H, 7.90%; N, 9.09%.

EXAMPLE 2

2,3-Dihydro-2,2,9-trimethyl-1H-pyrrolo[1,2-a]indol-1-amine Hydrochloride

[(I): $R^1=R^2=$—H; $R^3=R^4=$—CH$_3$]

A solution of mesylchloride (458 mg, 4 mmole) in pyridine (2 mL) was added dropwise at 0° C. to a solution of 2,3-dihydro-2,2,9-trimethyl-1H-pyrrolo[1,2-a]indole-1-ol, prepared by the process of Example 1, Step 3, (430 mg, 2 mmole) in the same solvent (15 mL) under exclusion of moisture. The reaction mixture was stirred for 30 minutes at 0° C. and 30 minutes at 25° C. A solution of pyrrolidine (2.3 g, 32 mmole) in pyridine (5 mL) was added dropwise at 0° C. The mixture was stirred at ambient temperature overnight. The solvent was evaporated to near-dryness in vacuo, and the residue dissolved in methylene chloride (50 mL). This solution was washed with 5% sodium carbonate (2×30 mL) and brine (50 mL). The organic layer was dried over MgSO4, filtered, and evaporated to dryness in vacuo. The obtained residue (810 mg) was chromatographed on silica gel (40 g). Elution with chloroform afforded 160 mg (37%) of product. The monohydrochloride salt was prepared in acetonitrile with ethanolic hydrochloric acid, then crystallized from ethanol, acetonitrile, and ether, m.p. 242.5°–245° C., as a creamy white powder.

IR (KBr): 3440 (broad), 2970, 2880, 2620, 1610, 1540, 1460, 1385, 740 cm$^{-1}$.

UV (MeOH): λmax 226, 277.5/ε=18275, 6600.

NMR (DMSO-d$_6$): δ 1.14 and 1.32 (singlets, 3H+3H, gem. CH$_3$), 2.35 (s, 3H, CH$_3$-9), 3.86 and 4.13 (doublets, J$_{gem}$=10 Hz, 1H+1H, H-3), 4.43 (br s, 1H, H-1), 7.07 (t, J=8 Hz, 1H, H-7), 7.18 (t, J=8Hz, 1H, H-6), 7.36 (d, J=8 Hz, 1H, H-5), 7.57 (d, J=8 Hz, 1H, H-8), 8.67 (broad, 3H, NH$_3$+).

MS (relative intensity, fragment) m/e: 214 (19, M+), 197 (2.5, M-NH$_3$), 158 (100, M-isobutylene).

Calculated: C, 67.05%; H, 7.64%; N, 11.17%. Found: C, 66.74%; H, 8.05%; N, 11.20%.

EXAMPLE 3

2,3-Dihydro-9-methyl-1-(1-pyrrolidinyl)-1H-pyrrolo[1,2-a]indole Hydrochloride

[(I): R$^1$ and R$^2$=1-pyrrolidinyl; R$^3$=R$^4$=—H]

2,3-Dihydro-9-methyl-1H-pyrrolo[1,2a]indol-1-one, prepared by the process of Example 1, Step 1, (120 mg, 0.65 mM) 5N methanolic HCl (0.26 mL, 1.3 mM), and sodium cyanoborohydride (46 mg, 0.73 mM) were added to a stirring solution of pyrrolidine (0.34 mL, 4 mM) in methanol (5 mL). The resulting suspension was stirred at room temperature protected from moisture for ~44 hours, acidified to pH 1–2 with concentrated HCl (aq), stirred at room temperature for an additional ½ hour. The solvent was removed in vacuo, and the residue partitioned between water (10 mL) and ethyl acetate (2×5 mL). The aqueous layer was basified to pH 10–11 with 10% sodium hydroxide (aq) and extracted with chloroform (3×10 mL). The combined chloroform extracts were dried over MgSO4, filtered, and evaporated to dryness in vacuo. The dark brown oily residu (124 mg) was flash chromatographed on silica gel (3.7 g), using 4% methanol in chloroform as eluent, to yield 70 mg (45%) of product as an amber colored oil.

NMR (CDCl$_3$): δ 1.77 (m, 4H, CH$_2$ of pyrrolidine), 2.35 (s, 3H, CH$_3$), 2.66 (broad m, 6H, CH$_2$-N and CH$_2$-2), 4.00 and 4.18 (multiplets, 1H+1H, CH$_2$-3), 4.21 (m, 1H, CH-1), 7.07 and 7.15 (triplets, J=8 Hz, 1H+1H, H-6 and H-7), 7.21 (d, J=8 Hz, 1H, H-5), 7.53 (d, J=8 Hz, 1H, H-8).

MS m/e: 240 (17%), 170 (100%).

EXAMPLE 4

2,3-Dihydro-9-methyl-1H-pyrrolo[1,2-a]indol-1-ol

Sodium borohydride (1.368 g, 36 mmole) was added portionwise to a solution of 2,3-dihydro-9-methyl-1H-pyrrolo[1,2-a]indol-1-one, prepared by the process of Example 1, Step 1, (2.22 g, 12 mmole) in methanol (200 mL). The reaction mixture was stirred at 25° C. for 2 hours, evaporated to near-dryness, and the residue suspended in water (150 mL). The product was extracted with chloroform (3×75 mL), and the combined organic layer dried over MgSO4, filtered, and evaporated to dryness. The residue was crystallized from ether to afford 1.32 g (59%) of product, m.p. 118.5°–120° C., as an off-white solid.

NMR (CDCl$_3$): δ 1.72 (br, s, 1H, OH), 2.36 (s, 3H, CH$_3$-9), 2.46–2.62 (m, 1H, H-2), 2.80–2.94 (m, 1H, H-2), 4.01–4.25 (m, 2H, H-3), 5.36 (br s, 1H, H-1), 7.04–7.24 (m, 3H, Ar-H), 7.54 (d, J=8 Hz, 1H, H-8).

MS (relative intensity, fragment) m/e: 187 (100, M+), 170 (83, M-OH).

EXAMPLE 5

2,3-Dihydro-9-methyl-1H-pyrrolo[1,2-a]indol-1ol is used for the production of compounds of formula (I) wherein R$^3$ and R$^4$ are hydrogen. The process is carried out according to Example 1, Step 4, or Example 2.

The compounds of formula (I) have been subjected to pharmaceutical tests which demonstrated protection against anoxia-induced lethality in mice and prevention of scopolamine-induced memory impairment in rats.

ANOXIA-INDUCED LETHALITY TEST IN MICE

The anoxia-induced lethality test in mice evaluates the activity of drugs which protect the animal from deleterious effects of oxygen-lack, such as occurs in conditions of cerebral ischemia. Activity is measured as the survival rate in mice exposed to 100% nitrogen for 80 seconds, a procedure which is lethal to 95% of untreated animals.

Test compounds are dissolved in water, or suspended in 0.2% aqueous Tween 80 and are administered i.p., 30 minutes prior to testing. Several doses and a vehicle control are tested, with 8 mice receiving each dose.

Male, CD-1 mice weighing 18–20 g are used. Mice are held separately within a cage in a modified plastic, air-tight desiccator which is connected to a tank of compressed 100% nitrogen gas.

Delivery of the anoxic gas is controlled by means of a toggle valve, and exposure is terminated by rapidly removing the mice from the desiccator. All operations are timed with a stopwatch. Drugs which reduce the anoxia-induced lethality solely by lowering body temperature are excluded.

| PROTECTION FROM ANOXIA-INDUCED LETHALITY IN MICE | | |
|---|---|---|
| Example # | Dose (mg/kg i.p.) | % protection |
| 1 | 50 | 75 |
| 2 | 50 | 100 |

We claim:
1. A compound of the structure (I)

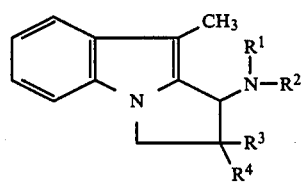

wherein $R^1$ and $R^2$ are independently selected from the group consisting of hydrogen, lower alkyl containing 1 to 4 carbon atoms, or $R_1$ and $R_2$ are joined together to form a heterocyclic amine radical, selected from the group consisting of pyrrolidinyl and piperidinyl; $R^3$ and $R^4$ represent hydrogen or lower alkyl containing 1 to 4 carbon atoms; and the pharmaceutically acceptable acid addition salts thereof.

2. A compound according to claim 1 wherein $R^1$ and $R^2$ are independently hydrogen, methyl, ethyl, propyl, or isopropyl; or $R^1$ and $R^2$ are joined together to form pyrrolidinyl, or piperidinyl; $R^3$ and $R^4$ are methyl; and the pharmaceutically acceptable acid addition salts thereof.

3. A compound according to claim 2 wherein $R^1$ and $R^2$ are hydrogen or methyl; or $R^1$ and $R^2$ are joined together to form pyrrolidinyl; $R^3$ and $R^4$ are both methyl; and the pharmaceutically acceptable acid addition salts thereof.

4. The compound according to claim 3 designated 2,3-dihydro-2,2,9-trimethyl-1H-pyrrolo[1,2-a]indol-1-amine hydrochloride, and the pharmaceutically acceptable salt thereof.

5. The compound according to claim 3 designated 2,3-dihydro-2,2,9-trimethyl-1-(1-pyrrolidinyl)-1H-pyrrolo[1,2-a]indole hydrochloride, and the pharmaceutically acceptable acid addition salts thereof.

6. A composition useful for the treatment of lethal effects of oxygen lack due to cerebral ischemia, transient ischemia attacks, stroke or multi-infarct dementia containing an effective amount of a compound as claimed in claim 1, or a pharmaceutically acceptable salt thereof, in association with a pharmaceutically acceptable excipient.

7. A method for the treatment of lethal effects of oxygen lack due to cerebral ischemia, transient ischemia attacks, stroke or multi-infarct dementia which comprises administering to a patient requiring such therapy an effective amount of a compound of formula (I) specified in claim 1, or a pharmaceutically acceptable acid addition salt thereof.

* * * * *